(12) United States Patent
Pavlik

(10) Patent No.: US 11,813,573 B2
(45) Date of Patent: *Nov. 14, 2023

(54) PLUNGER PUMPING ARRANGEMENT FOR A HOLLOW FIBER FILTER

(71) Applicant: REPLIGEN CORPORATION, Waltham, MA (US)

(72) Inventor: Rudolf Pavlik, Dover, MA (US)

(73) Assignee: Repligen Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,077

(22) Filed: Jul. 20, 2022

(65) Prior Publication Data

US 2022/0355251 A1 Nov. 10, 2022

Related U.S. Application Data

(63) Continuation of application No. 17/014,485, filed on Sep. 8, 2020, now Pat. No. 11,426,697, which is a
(Continued)

(51) Int. Cl.
*B01D 63/02* (2006.01)
*B01D 69/08* (2006.01)
(Continued)

(52) U.S. Cl.
CPC .............. *B01D 63/02* (2013.01); *B01D 29/11* (2013.01); *B01D 29/908* (2013.01); *B01D 35/26* (2013.01);
(Continued)

(58) Field of Classification Search
CPC ...... B01D 29/908; B01D 29/11; B01D 35/26; B01D 37/04; B01D 69/08; B01D 29/50; B01D 29/52; B01D 29/88; B01D 29/90; B01D 29/92; B01D 35/30; B01D 35/301; B01D 61/18; B01D 63/02; B01D 63/06; B01D 2201/20; B01D 2201/202; B01D 2201/204; B01D 2201/54; B01D 2221/10; B01D 2311/06; B01D 2311/14; B01D 2311/16; B01D 2313/24; B01D 2313/243;
(Continued)

(56) References Cited

U.S. PATENT DOCUMENTS 5,268,093 A * 12/1993 Hembree .................. C02F 1/50
210/764
9,605,664 B2 * 3/2017 Seith ...................... F04B 9/105
(Continued)

*Primary Examiner* — Joseph W Drodge
(74) *Attorney, Agent, or Firm* — KDW Firm PLLC

(57) ABSTRACT

A fluid filtration assembly includes a filter housing having a first end for fluid connection with a fluid storage vessel. A filter cartridge is disposable within the filter housing, and a plunger pump is coupled at a second end of the filter housing. The plunger pump includes a housing having a rigid portion and a flexible portion. The flexible portion has a plunger-engaging portion for coupling to the plunger of an actuator. The flexible portion selectively movable with respect to the rigid portion via the actuator. The filter cartridge can be a hollow fiber filter. The plunger pump can be configured to induce alternating tangential flow in at least a portion of the assembly. The fluid filtration assembly can be provided as a disposable single-use arrangement.

19 Claims, 5 Drawing Sheets

Related U.S. Application Data continuation of application No. 15/856,210, filed on Dec. 28, 2017, now Pat. No. 10,799,816.

(51) Int. Cl.

| | | |
|---|---|---|
| *B01D 37/04* | (2006.01) | |
| *B01D 35/26* | (2006.01) | |
| *B01D 29/11* | (2006.01) | |
| *B01D 29/90* | (2006.01) | |
| *F04B 43/00* | (2006.01) | |
| *F04B 43/06* | (2006.01) | |
| *F04B 53/20* | (2006.01) | |
| *C12M 1/00* | (2006.01) | |
| *C12M 1/12* | (2006.01) | |
| *F04B 43/067* | (2006.01) | |

(52) U.S. Cl.
CPC ............. *B01D 37/04* (2013.01); *B01D 69/08* (2013.01); *C12M 25/02* (2013.01); *C12M 29/10* (2013.01); *F04B 43/0063* (2013.01); *F04B 43/0081* (2013.01); *F04B 43/067* (2013.01); *F04B 53/20* (2013.01); *B01D 2313/243* (2013.01); *B01D 2313/58* (2013.01); *B01D 2313/90* (2013.01)

(58) Field of Classification Search
CPC ............ B01D 2315/10; B01D 2317/04; B01D 2319/04; B01D 2321/205; B01D 2321/2083; B01D 2313/58; B01D 2313/90; C12M 29/10; C12M 25/02; C12M 1/126; C12M 29/16; C12M 33/14; C12M 41/48; C12M 47/12; F04B 9/00; F04B 9/02; F04B 9/08; F04B 9/10; F04B 9/103; F04B 9/109; F04B 19/02; F04B 19/022; F04B 49/00; F04B 49/007; F04B 49/02; F04B 49/10; F04B 49/12; F04B 49/20; F04B 2201/02; F04B 2201/0201; F04B 2201/0202; F04B 2201/0206; F04B 2201/0207; F04B 45/04; F04B 45/047; F04B 45/053; F04B 45/065; F04B 45/067; F04B 45/073; F04B 43/0054; F04B 43/0063; F04B 43/0072; F04B 43/0081; F04B 43/009; F04B 43/04; F04B 43/09; F04B 43/086; F04B 53/20; F04B 2205/00; F04B 2205/01; F04B 2205/03; F04B 43/067
USPC ...... 210/141, 143, 257.1, 257.2, 258, 321.6, 210/321.78, 321.79, 321.8, 321.87, 210/321.88, 321.89, 340, 416.1; 417/1, 417/92, 93, 95–98, 103, 212, 274, 313; 435/297.1, 297.4, 308.1
See application file for complete search history.

(56) References Cited

U.S. PATENT DOCUMENTS

| | | | | |
|---|---|---|---|---|
| 10,166,497 | B1* | 1/2019 | Pavlik | B01D 29/908 |
| 10,799,816 | B2* | 10/2020 | Pavlik | B01D 69/08 |
| 11,426,697 | B2* | 8/2022 | Pavlik | B01D 63/02 |
| 2002/0094285 | A1* | 7/2002 | Paolini | F04B 43/043 |
| | | | | 417/413.1 |
| 2005/0167346 | A1* | 8/2005 | Johnson | B01D 61/14 |
| | | | | 210/321.66 |
| 2007/0163943 | A1* | 7/2007 | Collins | B01D 63/021 |
| | | | | 210/473 |
| 2013/0270165 | A1* | 10/2013 | Shevitz | C12M 41/40 |
| | | | | 210/205 |
| 2015/0204322 | A1* | 7/2015 | Iund | F04D 15/0094 |
| | | | | 175/48 |

* cited by examiner

PLUNGER PUMPING ARRANGEMENT FOR A HOLLOW FIBER FILTER

CROSS REFERENCE TO RELATED APPLICATION

This application is a continuation of U.S. nonprovisional patent application Ser. No. 17/014,485 filed Sep. 8, 2022, which is a continuation of U.S. nonprovisional patent application Ser. No. 15/856,210, filed Dec. 28, 2017, now U.S. Pat. No. 10,799,816, entitled "Plunger Pumping Arrangement for a Hollow Fiber Filter," the entirety of which applications are incorporated by reference herein. This application is also related to U.S. nonprovisional patent application Ser. No. 15/882,285, filed Jan. 29, 2018, now U.S. Pat. No. 11,166,497.

BACKGROUND OF THE DISCLOSURE

Field of the Disclosure

Embodiments of the disclosure relate generally to filtration systems, and more particularly to an alternating tangential flow filtration unit that includes a housing and a directly driven plunger pump.

Discussion of Related Art

Filtration is typically performed to separate, clarify, modify, and/or concentrate a fluid solution, mixture, or suspension. In the biotechnology, pharmaceutical, and medical industries, filtration is vital for the successful production, processing, and analysis of drugs, diagnostics, and chemicals as well as many other products. As examples, filtration may be used to sterilize fluids and to clarify a complex suspension into a filtered "clear" fraction and an unfiltered fraction. Similarly, constituents in a suspension may be concentrated by removing or "filtering out" the suspending medium. Further, with appropriate selection of filter material, filter pore size and/or other filter variables, many other specialized uses have been developed. These uses may involve selective isolation of constituents from various sources, including cultures of microorganisms, blood, as well as other fluids that may be solutions, mixtures, or suspensions.

Biologics manufacturing processes have advanced through substantial process intensification. Both eukaryotic and microbial cell culture to produce recombinant proteins, virus-like particles (VLP), gene therapy particles, and vaccines now include cell growth techniques that can achieve 100e6 cells/ml or higher. This is achieved using cell retention devices that remove metabolic waste products and refresh the culture with additional nutrients. One of the most common means of cell retention is to perfuse a bioreactor culture using hollow fiber filtration using alternating tangential flow (ATF). Commercial and development scale processes use a device that controls a diaphragm pump to perform ATF through a hollow fiber filter.

Diaphragm pumps include a pump housing separated into first and second interior chambers by an internal flexible diaphragm. The pump is actuated by feeding compressed air into the first chamber of the pump via a gas inlet, filling the first chamber with the gas, and forcing the diaphragm to expand the first chamber and to move fluid in the second chamber so that it passes through the filter an into, for example, an attached bioreactor vessel. When the gas is drawn back through the gas inlet, such as by a vacuum source, the diaphragm is drawn towards the gas inlet, which causes the first chamber to decrease in volume, and draws flow from the vessel through the filter and into the expanding second chamber. This action can be repeated, drawing fluid back and forth from the vessel, through the filter, and second chamber, thereby causing an alternating flow tangentially through the filter.

One problem with using a diaphragm pump to control flow through the filter is that it requires a source of compressed gas and vacuum utilities, including related hoses and generators, in order to actuate the pump. In addition, because the activating gas (e.g., air) is compressible, there can be an undesirable activation delay until sufficient pressure builds up in the first chamber to push the diaphragm upwards to move fluid out of the second chamber and through the filter. This activation delay can adversely impact overall process efficiency. It would, therefore, be desirable to provide a simplified pumping arrangement that eliminates the deficiencies of diaphragm pump systems.

SUMMARY OF THE DISCLOSURE

A fluid filtration assembly is disclosed, including a filter housing having a first end for fluid connection with a fluid storage vessel, a filter cartridge disposable within the filter housing, and a plunger pump coupled at a second end of the filter housing. The plunger pump includes a housing having a rigid portion and a flexible portion. The flexible portion has a plunger-engaging portion for coupling to the plunger of an actuator, and is selectively movable with respect to the rigid portion via the actuator. The flexible portion of the housing is movable between first and second positions via the actuator, where moving the flexible portion from the first position to the second position causes fluid in the housing to be expelled into the filter housing. Moving the flexible portion from the second position to the first position causes fluid in the filter housing to be drawn into the housing.

In some embodiments, the plunger-engaging portion has a recess for receiving a rod portion of the actuator portion. The plunger-engaging portion is aligned with a center of the filter housing. The flexible portion can be bell-shaped, accordion-shaped or bellows-shaped. The rigid portion and the flexible portion each can have respective radially extending flanges, where opposing face surfaces of the radially extending flanges contact each other and are clamped together via clamp portion. The flexible portion can, in some embodiments, be connected to the rigid portion via overmolding of the flexible portion or by a mechanical connection. The actuator comprises a linear drive mechanism coupleable to the plunger pump. The rigid portion of the housing can be integrally formed with the filter housing, or it can be clamped to the filter housing. The filter cartridge can be a hollow fiber filter or a membrane filter. The plunger pump can be configured to generate alternating tangential flow of the fluid between the filter housing and the plunger pump.

A fluid filtration system is disclosed, including a process vessel, a filter housing having a first end in fluid communication with the process vessel, a filter cartridge disposable within the filter housing, and a plunger pump coupled at a second end of the filter housing. The plunger pump includes a housing having a rigid portion and a flexible portion. The flexible portion has a plunger-engaging portion for coupling to the plunger of an actuator. The flexible portion is selectively movable with respect to the rigid portion via the actuator. The flexible portion of the housing is movable between first and second positions via the actuator, where moving the flexible portion from the first position to the second position causes fluid in the housing to be expelled into the filter housing and the process vessel. Moving the flexible portion from the second position to the first position causes fluid in the process vessel to be drawn into the filter housing.

In some embodiments, the plunger-engaging portion includes a recess for receiving a rod portion of the actuator portion, the plunger-engaging portion being aligned with a center of the filter housing. The flexible portion can be bell-shaped, accordion-shaped or bellows-shaped. A linear encoder or other travel measuring device may be coupled to the plunger of the actuator for determining a position of the plunger. A controller may be coupled to the actuator, and may control movement of the plunger of the actuator to controllably move the flexible portion of the housing. The controller comprises a processor executing instructions for controlling a stroke distance and a stroke rate of the plunger. The controller can further includes memory associated with the processor, the memory including predetermined stroke distance and stroke rate values associated with specific filter and pump sizes. The filter cartridge can be a hollow fiber filter or a membrane filter. The plunger pump can be configured to generate alternating tangential flow of the fluid between the filter housing and the plunger pump.

A fluid filtration system, comprising first and second process vessels, a first filter housing having a first end in fluid communication with the first process vessel; a second filter housing having a first end in fluid communication with the second process vessel; a first plunger pump coupled to a second end of the first filter housing; a second plunger pump coupled to a second end of the second filter housing; wherein each of the first and second plunger pumps includes a housing having a rigid portion and a flexible portion, the flexible portion having a plunger-engaging portion for coupling to the plunger of an actuator, the flexible portion selectively movable with respect to the rigid portion via the actuator, a controller in communication with the actuator for simultaneously actuating the first and second plunger pumps to cycle fluid between the first and second plunger pumps and the first and second process vessels.

The controller can include a processor executing instructions for controlling a stroke distance and a stroke rate of the first and second plunger pumps. The controller can further include memory associated with the processor, the memory including predetermined stroke distance and stroke rate values associated with specific filter and pump sizes. The first and second plunger pumps can be configured to generate alternating tangential flow of the fluid between the first and second filter housings and the first and second plunger pumps, respectively.

BRIEF DESCRIPTION OF THE DRAWINGS

The accompanying drawings illustrate preferred embodiments of the disclosed method so far devised for the practical application of the principles thereof, and in which.

DESCRIPTION OF EMBODIMENTS

Figure 1:
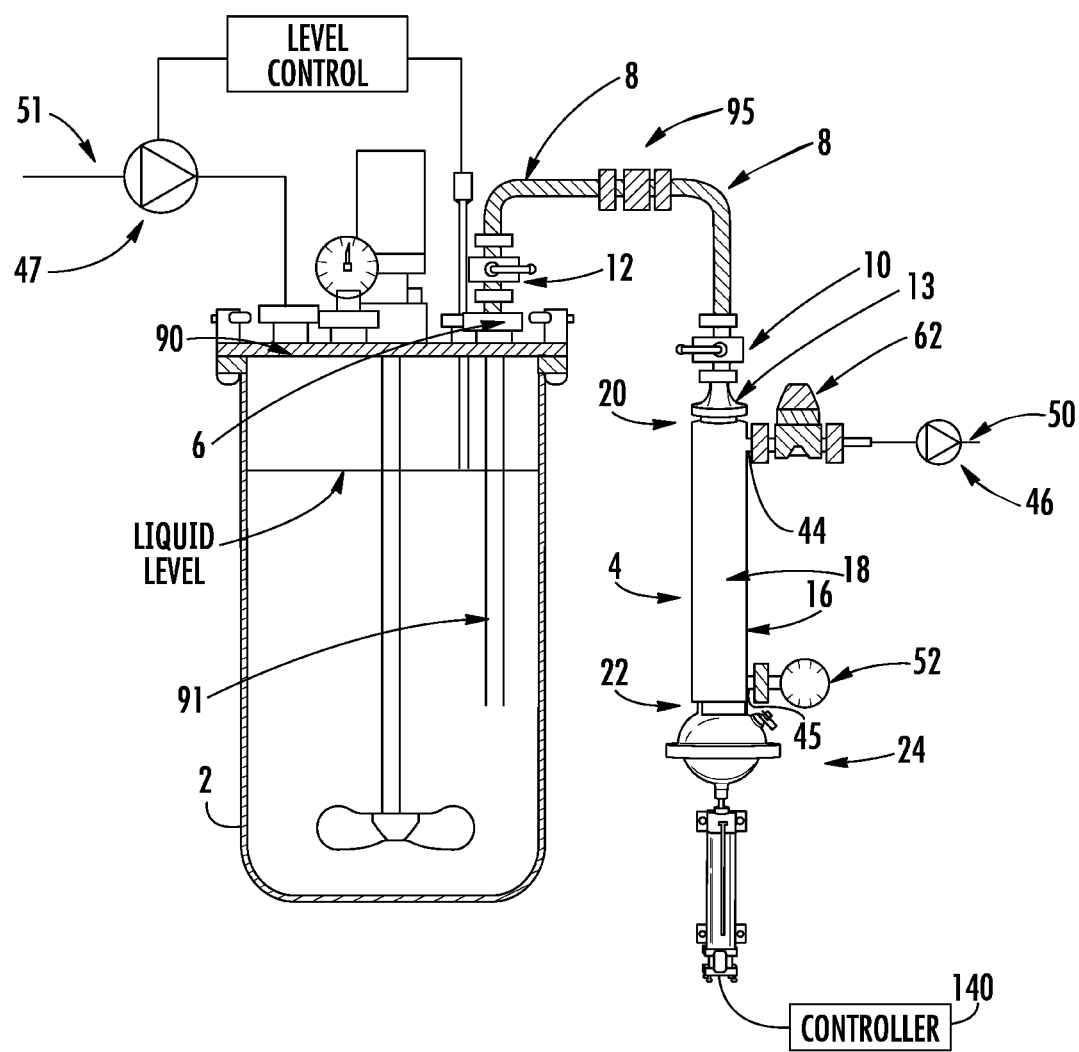
FIG. 1 is a schematic view of an alternating tangential flow filtration system according to the disclosure.

A fluid filtration system is disclosed, comprising a fluid storage vessel, connecting piping or tubing for directing fluid from the vessel through a filter, and a plunger pump which moves the fluid in alternating directions through the filter. The system can be employed for conducting a rapid, low sheer, Alternating Tangential Flow (ATF) of fluid through the filter, which in some embodiments is a hollow fiber filter. Such a system has applications in perfusion of cultured animal cells as well as other varied filtration applications.

In some embodiments, a single use filter housing includes a filter and plunger pump as an integral assembly for filtering fluid stored in the vessel. The entire assembly can be single use, made from sterilizable materials with aseptic connectivity. The single use assembly can be sterilized using any of a variety of appropriate technologies, including gamma irradiation sterilization, ethylene oxide sterilization, and the like. A plunger activation system can include a controller and a two-directional movement device such as a servo motor, cam, pneumatic or electrical actuator. It will be appreciated that the plunger activation system, such as servo motor, cam, pneumatic or electrical actuator, will be connected to the plunger pump via a connection/disconnection coupling, and will be applied at the point of use. Thus, the plunger activation system will not be sterilized.

The plunger pump has a liquid side which is sealed to the filter housing hemisphere and an external side which has a mechanical connection coupling positioned symmetrically in the center of a plunger. The plunger material can be a rubbery, medical grade thermoplastic material, a silicone or other appropriate elastomeric material. The plunger movement in a "pull" cycle generates suction (i.e., drawing liquid toward, or into, the pump), and in a "push" cycle provides liquid extraction or expulsion (i.e., pushing liquid away from, or out of, the pump). The stroke distance of the plunger pump in the pull and push mode can be predetermined and/or adjusted as appropriate to accommodate the particular size of the filter assembly. In some embodiments the stroke distance can be automatically controlled by a device such as a linear encoder.

The actuation system and the plunger can be universal for all available sizes of filter assemblies. Confirmation of pump size can, in some embodiments, automatically reset the stroke distance to be appropriate for a particular filter assembly size. Since travel distance for each pump size is different, the actuation travel will be set for the largest pump size, which requires the longest stroke. Any other pump size will have a shorter stroke, and thus, the travel will be adjusted based on a specific pump stroke requirement. Pump stroke for the smaller filter assemblies will start from the end "push" position, and distance of the "pull" travel will correspond with the appropriate volume required by the particular filter size.

Speed of movement can be part of a separate setting entered directly into a control module by a user, or it can be dictated by a selectable recipe. One plunger "push" and "pull" motion represents the pump cycle. The number of cycles per minute represents plunger pump flow, which is typically measured in liters per minute. Greater or fewer cycles per minute will provide higher or lower pump flow. The desired pump flow can be entered manually or can be a part of a process recipe.

Referring now to FIG. 1 a fluid filtration system includes a process vessel 2 connected via a fluid connector to a pump and filter assembly 4. The vessel 2 may be any suitable container for housing a fluid to be filtered. For example, it may be a bioreactor, a fermentor or any other vessel, nonexclusively including vats, barrels, tanks, bottles, flasks, containers, and the like which can contain liquids. The process vessel 2 may be composed of any suitable material such as plastic, metal such as stainless steel, glass, or the like. The fluid connector serves to fluidly couple the process vessel 2 to the pump and filter assembly 4.

The fluid connector may comprise a vessel port 6 coupled to the process vessel 2, and an appropriate section of piping 8 which is in turn is connected to the entrance end of the pump and filter assembly 4. The vessel port 6 can be any appropriate sanitary, leak-proof fittings known in the art such as a compression, standard Ingold or a sanitary type fitting. The piping 8 can alternatively include tubes, hoses, hollow joint assemblies, and the like. In addition, the piping 8 can include appropriate valves 10 and 12 for selectively isolating, or allowing, flow between the vessel 2 and the pump and filter assembly 4.

In the illustrated embodiment, a vessel port 6 is provided through a head plate 90 of the process vessel 2. A dip tube 91 is used to connect to the liquid in the process vessel 2 to piping 8. It will be appreciated that piping 8 need not be rigid and flexible connection 95 may facilitate making and breaking connection between the vessel 2 and the filter assembly 4. In some embodiments, filtered harvested liquid can be collected from the filter assembly 4 through line 50. The harvested liquid may be restored by a level control mechanism that activates an additional pump 47 to pump liquid into the vessel through line 51.

The pump and filter assembly 4 includes a filter housing 16 that holds a filter element cartridge 18. The housing 16 can include a fluid harvest port 44 suitable for removing filtered fluid from the housing. A harvest line 50 can be coupled to the fluid harvest port 44, and can include a valve 62 and a filtrate pump 46 for controlling the removal of filtered fluid from the system. Pressure in the housing 16 may be monitored by a pressure valve or transducer 52 coupled to the housing via a monitoring port 45.

The pump and filter assembly 4 can include a filter housing 16 and a plunger pump 24 coupled thereto. The filter housing can have an entrance end 20 and an exit end 22. The entrance end 20 can be attached to the piping 8, for example, via valve 10 and adapter 13. The exit end 22 can be connected to the plunger pump 24 as will be described in greater detail later.

The filter housing 16 can be made from plastic, metal, such as stainless steel, glass, and the like. Suitable removable filter element cartridges 18 (for reusable filter housings) or complete, permanent housings (for single use systems) include hollow fiber filters, screen filters, and the like. In one non-limiting example embodiment, the filter element cartridge 18 is a hollow fiber filter. According to the disclosure, pump and filter assembly 4 can be configured for single use (i.e., disposable), with the filter housing 16, filter cartridge 18 and plunger pump 24 provided together as an integral assembly.

Various advantages exist in providing the pump and filter assembly 4 as a single-use (disposable) assembly. For example, the assembly can be set up with minimal handling and do not require cleaning or sterilization by the user, since the components are supplied sterile and in a form ready to use with minimal preparation and assembly. This can result in cost savings due to reduced labor and handling by the user along with elimination of a long autoclave cycle. Furthermore, at the end of their use, the assembly can be readily discarded without cleaning. A disposable assembly reduces risk of contamination and assembly by operators, and do not require lengthy validation procedures for operation/sterilization. The components of the assembly also can be lighter and easier to transport, and are less expensive and take up less storage space compared to stainless steel or glass units.

Figure 2:
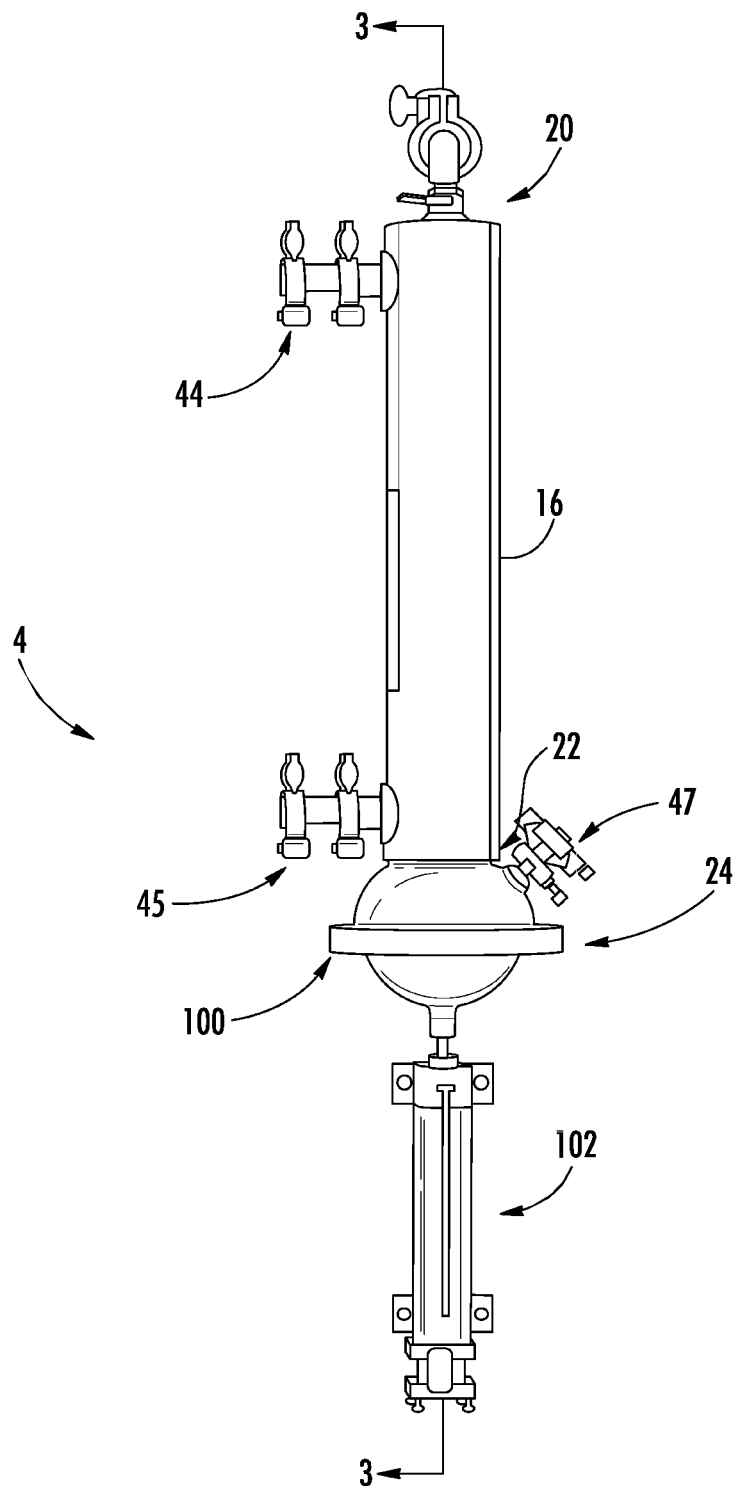
FIG. 2 is a side view of a pump and filter assembly for use with the system of FIG. 1.

FIG. 2 illustrates an example pump and filter assembly 4 including filter housing 16 enclosing a filter (not shown) and a plunger pump 24. In one non-limiting example embodiment, the pump and filter assembly 4 is a single use integral assembly for filtering fluid stored in the process vessel 2. The pump and filter assembly 4 can include an entrance end 20, an exit end 22, a fluid harvest port 44, and a monitoring port 45 for coupling a pressure valve or transducer as previously mentioned. A sample port 49 can be provided for coupling a sampler valve (not shown) to the filter housing 16.

A sampler valve may be used for a variety of purposes including sampling the quality of the fluid in the plunger pump 24, injecting or expelling liquid or gas into and out of the pump, and injecting sterilizing steam into the system and/or removing resulting steam condensate from the system. For example, the sampler valve may be suitable for injecting air into the system to expel liquid from the system into the process vessel prior to detachment of the filter system from the process vessel; conversely, it may be used to purge air from the system prior to initiating alternating tangential flow.

The plunger pump 24 can include a housing portion 100 and an actuator portion 102. As shown in greater detail in FIGS. 3 and 4, the housing portion 100 may include a rigid portion 104 and a flexible portion 106 coupled together. The flexible portion 106 may also be coupled to the actuator portion 102 so that the flexible portion 106 is movable with respect to the rigid portion 104 in response to activation of the actuator portion. The actuator portion 102 may include a cylinder housing 103, and a driven rod portion 138 that is selectively movable within the cylinder housing. As will be described in greater detail below, a servo motor, cam, pneumatic or electrical actuator can be used to selectively move the rod portion 138 in the directions of arrows "A" and "B" to cause the plunger pump 24 to move fluid through the filter housing 16 in a desired manner.

Figure 3:
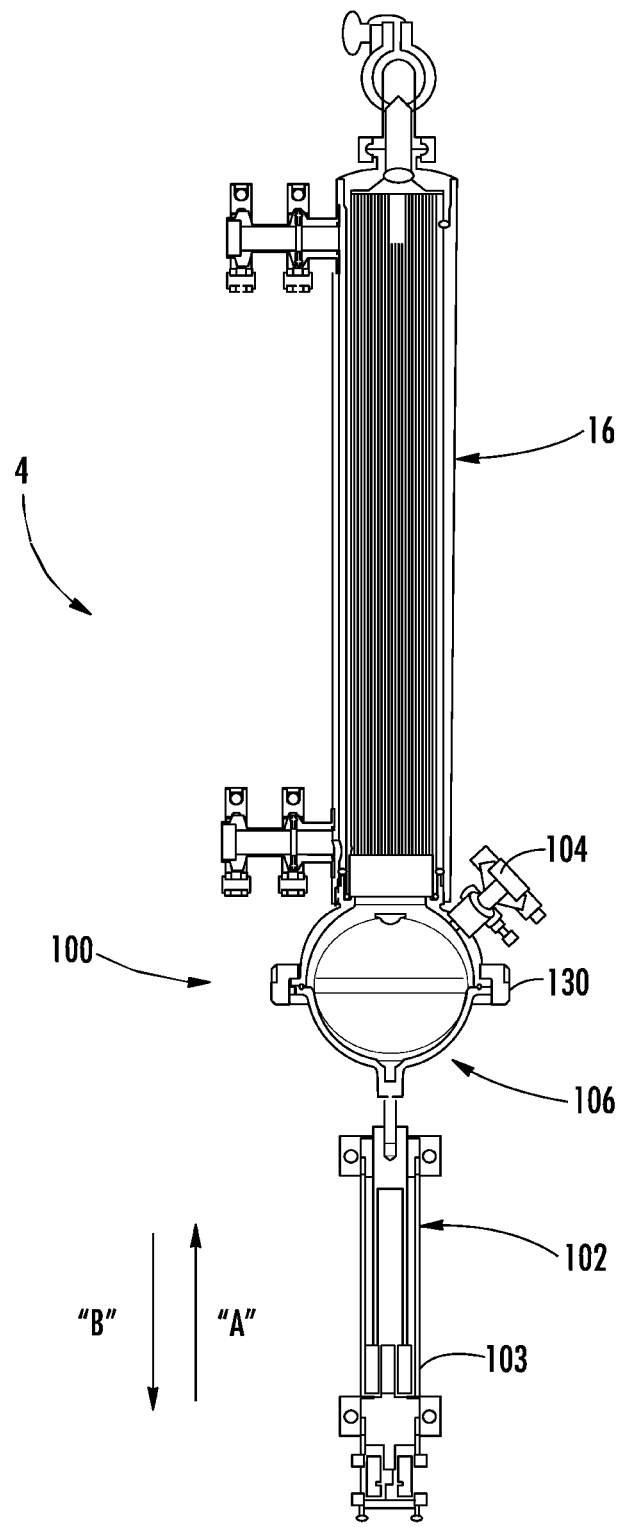
FIG. 3 is a cross-section view of the pump and filter assembly of FIG. 2 taken along line 3-3 of FIG. 2.
Figure 4:
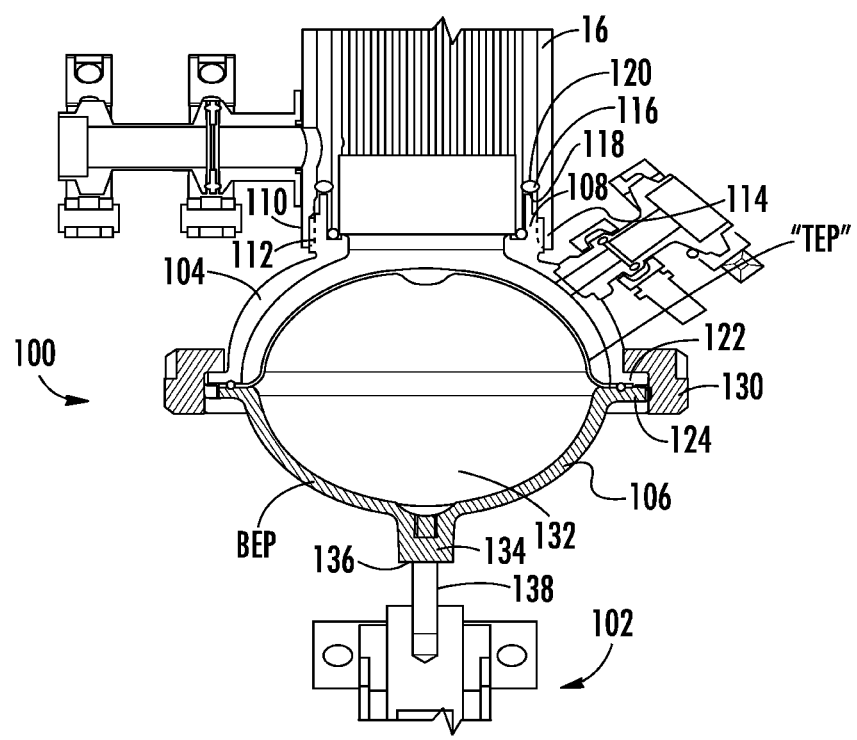
FIG. 4 is a partial detail view of the pump and filter assembly shown in FIG. 3.

As can be seen in FIGS. 3 and 4, an upper end 108 of the rigid portion 104 of the housing portion 100 is coupled to a lower end 110 of the filter housing 16 in a manner that allows fluid to flow freely therebetween. In the illustrated embodiment, the upper end 108 of the rigid portion includes external threads 112 sized and configured to mate with internal threads 114 of the lower end 110 of the filter housing 16. An O-ring 116 is disposed between an upper end surface 118 of the rigid portion 104 and a lower end surface 120 of the filter housing 16 to provide fluid-tight engagement between the two. It will be appreciated that although a threaded connection is disclosed, other coupling and sealing arrangements can be used without departing from the spirit of the disclosure. In addition, it is contemplated that the rigid portion 104 of the housing portion 100 can be formed as an integral part of the filter housing 16.

As best seen in FIG. 4, the rigid portion 104 and flexible portion 106 of the housing portion 100 can each be bell-shaped members that can be coupled together to provide the housing portion with a globe shape having an interior volume 132 defined by respective inner surfaces of the rigid and flexible portions. The rigid portion 104 and flexible portion 106 have respective radially extending flanges 122, 124. The combination of the flanges 122 and 124, corresponding "O" ring like feature of the flexible portion 106 of the plunger, and the durometer of the flexible portion guarantee an integral connection secured by a clamp (referred to as a "nut") 130. In some embodiments, the flexible portion 106 can be formed from an elastomer that is overmolded on the rigid portion 104, thus eliminating the need for a clamp portion.

The flexible portion 106 may have a bell, accordion or bellows shape. As will be appreciated, expansion or contraction of the flexible portion 106 can generate vacuum and pressure required to initiate movement of fluid between the plunger pump 24 and the process vessel 2. Friction between the internal plunger surfaces (liquid contact area) can be mitigated by the plunger shape design. For example, when the flexible portion 106 moves to each end position of the stroke (i.e., the bottom end position "BEP" and the top end position "TEP" explained below), the internal surfaces of the plunger will not be in contact.

The flexible portion 106 may include a plunger-engaging portion 134 disposed in or on a bottom surface thereof. The plunger-engaging portion 134 may include a recess 136 for receiving the rod portion 138 of the actuator portion 102. In the illustrated embodiment, the plunger-engaging portion 134 is aligned with a center of the filter housing 16. Thus arranged, movement of the actuator portion 102 in the direction of arrow "A" causes an even deformation of the flexible portion 106 with respect to the rigid portion 104.

As the actuator portion 102 drives the rod portion 138 in the direction of arrow "A" (i.e., toward the rigid portion 104), the flexible portion 106 deforms and moves toward the rigid portion. In one embodiment, the rod portion 138 is driven to move the flexible portion 106 from a bottom end position "BEP" to a top end position "TEP". As will be appreciated, when the flexible portion 106 is in the BEP, the interior volume 132 of the housing portion 100 is a first value, and when the flexible portion is in the TEP the interior volume of the housing portion 100 is a second value, where the second value is less than the first value. Thus, as the rod portion 138 moves the flexible portion 106 from the BEP to the TEP (i.e., the direction of arrow "A"), the flexible portion forces liquid contained in the housing portion 100 up into the filter housing 16 and back into the vessel 2. In reverse, when the rod portion 138 moves the flexible portion 106 from the TEP to the BEP (i.e., in the direction of arrow "B"), liquid is drawn from the vessel 2, through the filter cartridge 18 in the filter housing 16, and into the housing portion 100.

In some embodiments, the actuator portion 102, and thus operation of the plunger pump 24, can be automated via a controller 140. The controller may include an appropriate processor and associated memory (not shown). The processor may execute instructions for actuating the plunger pump 24 according to a desired set of cycle parameters (e.g., stroke distance, stroke rate). The actuator portion 102 an include a linear encoder (not shown) that can monitor the position of the rod portion 138 and provide associated position information to the processor and/or other component of the controller 140. The location of the rod portion 138 can be monitored throughout an entire actuation cycle of the plunger pump 24. Thus, the controller 140 can monitor the end positions (BEP and TEP) of the flexible portion 106, and can use this information to determine and/or control fluid volume displacement over a particular time period. Due to the mechanical engagement between the rod portion 138 and the flexible portion 106 of the pump 24, the stroke distance can be known with a relatively high degree of confidence at any point of the actuation process.

In some embodiments, the stroke distance (i.e., the distance that the rod portion 138 and the flexible portion 106 are moved in a given direction) can be preset by the controller and is dependent upon the size of the particular pump and filter assembly 4 used. Using the linear encoder of the actuator portion 102, the stroke distance can be appropriately controlled and confined to the predetermined value by the controller 140. In this manner, the controller 140 and actuator portion 102 can be used universally for all available sizes of pump and filter assemblies 4. Using an automatic stroke distance preset for each filter is a convenient way to prevent a short or over stroking the plunger.

Confirmation by the controller 140 of the size of a particular pump and filter assembly 4 may result in an automatic reset of the stroke distance. A stroke speed can be entered or otherwise set in the controller 140 either directly or dictated by a recipe or appropriate algorithm.

The connection between the actuator portion 102 and the controller 140 is illustrated as being hard wired, but it will be appreciated that the two may be wirelessly connected. The controller can have an interaction interface that can allow the user to control stroke distance, stroke movement profile, flow of the plunger pump 24 and control of any ancillary devices related to the functions of the filter assembly 4.

In use, the plunger pump 24 can generate an alternating tangential flow through the filter cartridge 18 when the flexible portion 106 is driven via the actuator portion 102. The plunger pump 24 can generate a reversible flow of liquid such as a culture suspension, back and forth, between the process vessel 2 and plunger pump 24. For example, flow from the interior volume 132 of the housing portion 100 through the filter cartridge 18 to the process vessel 2 is generated by moving the flexible portion 106 of the pump in the direction of arrow "A" (i.e., from the BEP to TEP). Movement of flexible portion 106 expels liquid from the interior volume 132 of the housing portion 100, moving the liquid towards the process vessel 2, and generating a tangential flow in one direction. Final, filtered product is removed through a port 44, for example, by a peristaltic pump. In the reverse, when the flexible portion 106 of the pump is moved in the direction of arrow "B" (i.e., from TEP to BEP), the pressure in the interior volume 132 of the housing portion 100 is decreased relative to the pressure in vessel 2. Thus, the flow path is reversed, and liquid flow from the process vessel 2 back to the interior volume 132 of the housing portion 100, generating tangential flow in the opposite direction. Final filtered product is removed through a port 44 by, for example, a peristaltic pump. Flow from pump 24 to the process vessel 2 and return from the process vessel 2 to the pump 24 completes one cycle.

The cycle rate and the flow rate between the plunger pump 24 and the process vessel 2 will depend primarily on the configuration of the pump and the control mechanism used to regulate the cycle.

Figure 5:
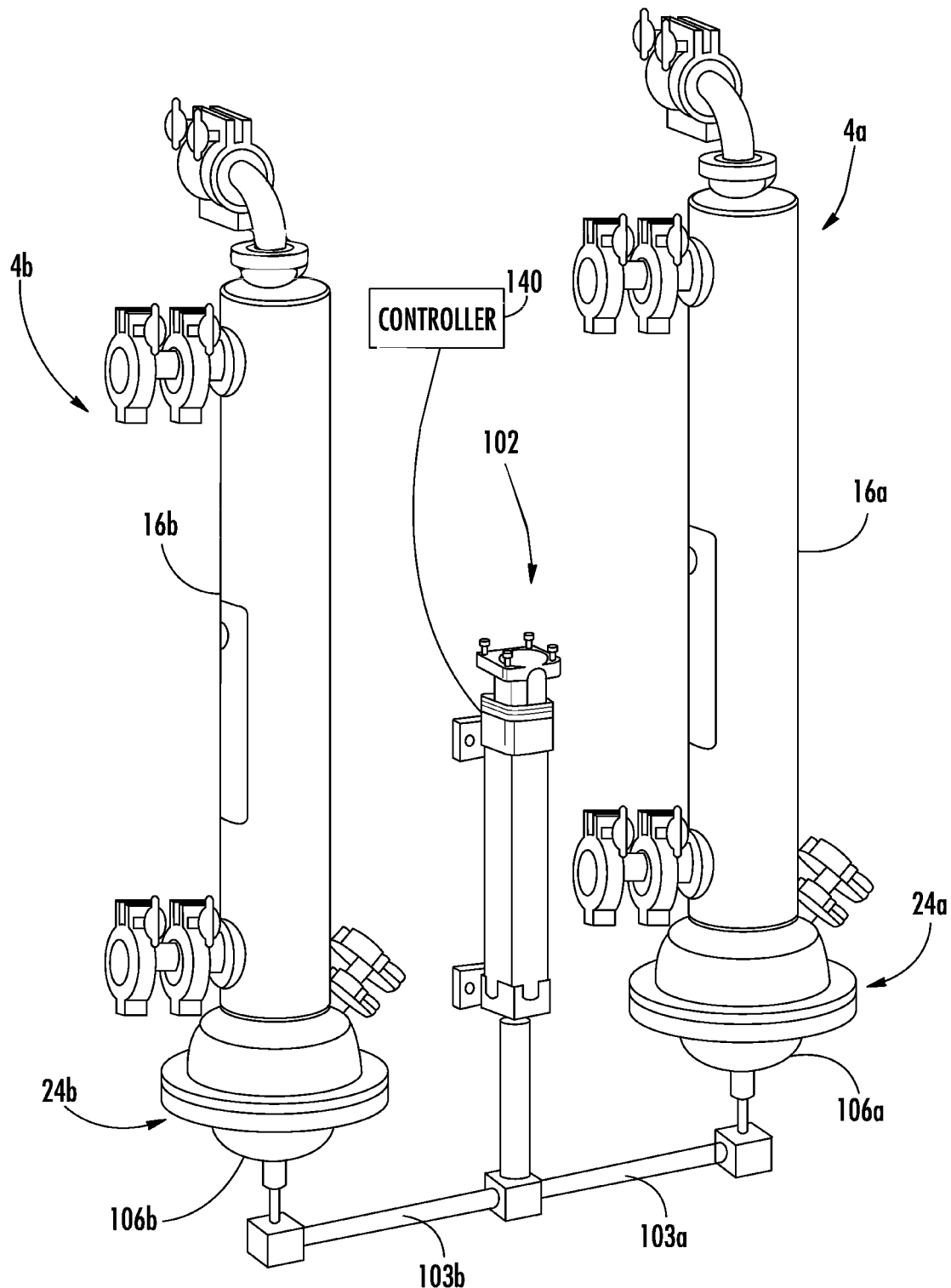
FIG. 5 is an isometric view of an alternative embodiment of a pump and filter assembly for use with the system of FIG. 1.

FIG. 5 shows a single actuator portion 102 used to simultaneously actuate a pair of pump and filter assemblies 4a, 4b, including pumps 24a, 24b, filter housings 16a, 16b, and respective filters (not shown). Although the illustrated embodiment shows a single actuator portion 102 for actuating two pump and filter assemblies 4a, 4b, it will be appreciated that a greater number of pump and filter assemblies could be controlled by a single actuator portion 102, which, in turn, can be controlled by a single controller. In this arrangement, a single actuator portion 102 is connected to rigid linkages 103*a*, 103*b* which are connected to the flexible portions 106*a*, 106*b* of the pumps 24*a*, 24*b* via connecting couplings in the manner previously described. Pumping actuation for this arrangement is identical to the actuation described in relation to FIGS. 1-4.

While the present arrangement has been disclosed with reference to certain embodiments, numerous modifications, alterations and changes to the described embodiments are possible without departing from the spirit and scope of the disclosed arrangement, as defined in the appended claims. Accordingly, it is intended that the present arrangement not be limited to the described embodiments, but that it has the full scope defined by the language of the following claims, and equivalents thereof.

What is claimed is:

1. A fluid filtration system, comprising:
   a process vessel;
   a filter housing having a first end fluidly communicating with the process vessel;
   a plunger pump coupled to a second end of the filter housing, the plunger pump comprising an actuator, the plunder pump including a plunger; and
   a controller in communication with the actuator, the controller configured to displace the plunger a linear distance in strokes;
   wherein the controller comprises a processor executing preset instructions to alter the linear distance of the plunger displacement depending on a size of the plunger pump and a size of the filter housing;
   wherein the controller comprises memory associated with the processor, the memory including at least one of predetermined stroke distance values and predetermined stroke rate values associated with a plurality of filter housing sizes and pump sizes; and
   wherein confirmation by the controller of a size of the pump of the system and a size of the filter housing of the system causes an automatic reset of the stroke distance for the plunger.

2. The fluid filtration system of claim 1, wherein the actuator includes a linear encoder for monitoring the displacement of the plunger and for providing associated position information to the controller.

3. The fluid filtration system of claim 2, wherein the linear encoder monitors a bottom end position and a top end position of the plunger and provides the bottom end position and a top end position information to the controller to determine and/or control fluid volume displacement by the plunger pump over a time period.

4. The fluid filtration system of claim 2, wherein a stroke speed of the plunger is provided to the controller directly or dictated by a recipe or algorithm.

5. The fluid filtration system of claim 1, wherein the processor executes preset instructions to determine a fluid volume displacement of the plunger pump.

6. The fluid filtration system of claim 1, wherein the processor executes preset instructions to control the plunger pump to generate alternating flow of fluid through the filter housing.

7. The fluid filtration system of claim 1, wherein the processor is programmed to execute instructions for actuating the plunger pump according to a predetermined set of cycle parameters.

8. The fluid filtration system of claim 7, wherein the set of cycle parameters comprises the stroke distance and a stroke rate.

9. A fluid filtration system, comprising:
   a filter housing having a first end comprising a first fluid line and a second end;
   a plunger pump coupled to the second end of the filter housing, the plunger pump comprising a rigid portion and a flexible plunger-engaging portion coupled to an actuator, the flexible plunger-engaging portion selectively movable with respect to the rigid portion via the actuator; and
   a controller in communication with the actuator, the controller configured to displace the plunger-engaging portion a linear distance;
   wherein the controller comprises a processor executing preset instructions to alter the linear distance of the plunger-engaging portion displacement depending on a size of the plunger pump and a size at the filter housing.

10. The fluid filtration system of claim 9, wherein the actuator includes a linear encoder for monitoring the distance of the plunger-engaging portion displacement and for providing associated position information to the controller.

11. The fluid filtration system of claim 10, wherein the linear encoder monitors a bottom end position and a top end position of the plunger-engaging portion and provides the bottom end position and the top end position information to the controller to determine and/or control an amount of fluid volume displacement by the plunger pump over a time period.

12. The fluid filtration system of claim 9, wherein a stroke speed of the plunger-engaging portion displacement is provided to the controller directly or dictated by a recipe or algorithm.

13. The fluid filtration system of claim 9, wherein the processor executes preset instructions to determine a fluid volume displacement of the plunger pump.

14. The fluid filtration system of claim 9, wherein the processor executes preset instructions to control the plunger pump to generate alternating flow of fluid through the filter housing.

15. The fluid filtration system of claim 9, wherein the controller comprises memory associated with the processor, and the plunger-engaging portion is displaced in strokes, the memory including at least one of predetermined stroke distance values and predetermined stroke rate values, associated with a plurality of filter housing sizes and pump sizes.

16. The fluid filtration system of claim 15, wherein confirmation by the controller of the size of the pump of the system and the size of the filter housing of the system causes an automatic reset of the stroke distance for the plunger-engaging portion.

17. The fluid filtration system of claim 9, wherein the processor is programmed to execute instructions for actuating the plunger pump according to a predetermined set of cycle parameters, and the plunger-engaging portion is displaced in strokes.

18. The fluid filtration system of claim 17, wherein the set of cycle parameters comprises the stroke distance and a stroke rate.

19. A fluid filtration system, comprising:
   a process vessel;
   a filter housing having a first end fluidly communicating with the process vessel;
   a plunger pump coupled to a second end of the filter housing, the plunger pump comprising an actuator, the plunger pump including a plunger; and
   a controller in communication with the actuator, the controller configured to displace the plunger a linear distance;

wherein the controller comprises a processor executing preset instructions to alter the linear distance of the plunger displacement depending on a size of the plunger pump and a size of the filter housing;

wherein the actuator includes a linear encoder for monitoring the displacement of the plunger and for providing associated position information to the controller; and wherein the linear encoder monitors a bottom end position and a top end position of the plunger and provides the bottom end position and the top end position information to the controller to determine and/or control an amount of fluid volume displacement by the plunger pump over a time period.

* * * * *